United States Patent [19]

Insall

[11] Patent Number: 5,443,518
[45] Date of Patent: Aug. 22, 1995

[54] KNEE POSITION INDICATOR

[75] Inventor: John N. Insall, Scarsdale, N.Y.

[73] Assignee: Zimmer, Inc., Warsaw, Ind.

[21] Appl. No.: 94,636

[22] Filed: Jul. 20, 1993

[51] Int. Cl.$^6$ ................................................ A61F 2/38
[52] U.S. Cl. ...................................................... 623/20
[58] Field of Search .......................................... 623/20

[56] References Cited

U.S. PATENT DOCUMENTS

| 3,837,009 | 9/1974 | Walker | 623/20 |
| 4,213,209 | 7/1980 | Insall | 623/20 |
| 5,326,363 | 7/1994 | Aikins | 623/20 |

OTHER PUBLICATIONS

Tekscan, Inc.-Product Description-Copyright 1989.

Primary Examiner—Randy C. Shay
Attorney, Agent, or Firm—Cary R. Reeves

[57] ABSTRACT

A tibial knee component includes reference marks to which a surgeon can reference the location of the point of contact between the tibial component and a femoral knee component. In one embodiment of the invention, the femoral component also includes reference marks to aid the surgeon in determining the contact point and to aid in orienting the knee in specific predetermined degrees of flexion.

4 Claims, 2 Drawing Sheets

KNEE POSITION INDICATOR

BACKGROUND OF THE INVENTION

The present invention relates to artificial knee joint components containing index marks to indicate the position of one component with respect to the other.

During knee joint replacement surgery it is desirable to know where the contact point between the femoral and tibial components lies relative to the anterior-posterior dimension of the tibia. This information can aid in aligning the components for proper location of the initial contact between the femoral and tibial components. It is also informative to know how the location of this contact point changes during flexion and extension of the knee joint. If the contact point shifts posteriorly several millimeters, known as rollback, and the posterior cruciate ligament (PCL) is intact, the PCL is causing at least some of the rollback and therefore is functional. A surgeon can then make informed decisions as to the appropriate type of implant, the balancing of soft tissue tension around the knee joint by carefully severing certain tissues, and the adjustment of component alignment. With prior knee joint components, both the implants themselves and the provisional implants used for size selection, there is no indicator to aid in quantifying contact point location or contact point change in location.

SUMMARY OF THE INVENTION

This invention provides a means for visualizing the contact point location and gauging its change in location with knee flexion and extension. The tibial component includes reference marks with which the surgeon can compare contact point location. In one embodiment of the invention, the femoral component also includes reference marks to aid the surgeon in determining the contact point and to aid in orienting the knee in specific predetermined degrees of flexion.

DETAILED DESCRIPTION OF THE INVENTION

Figure 1:
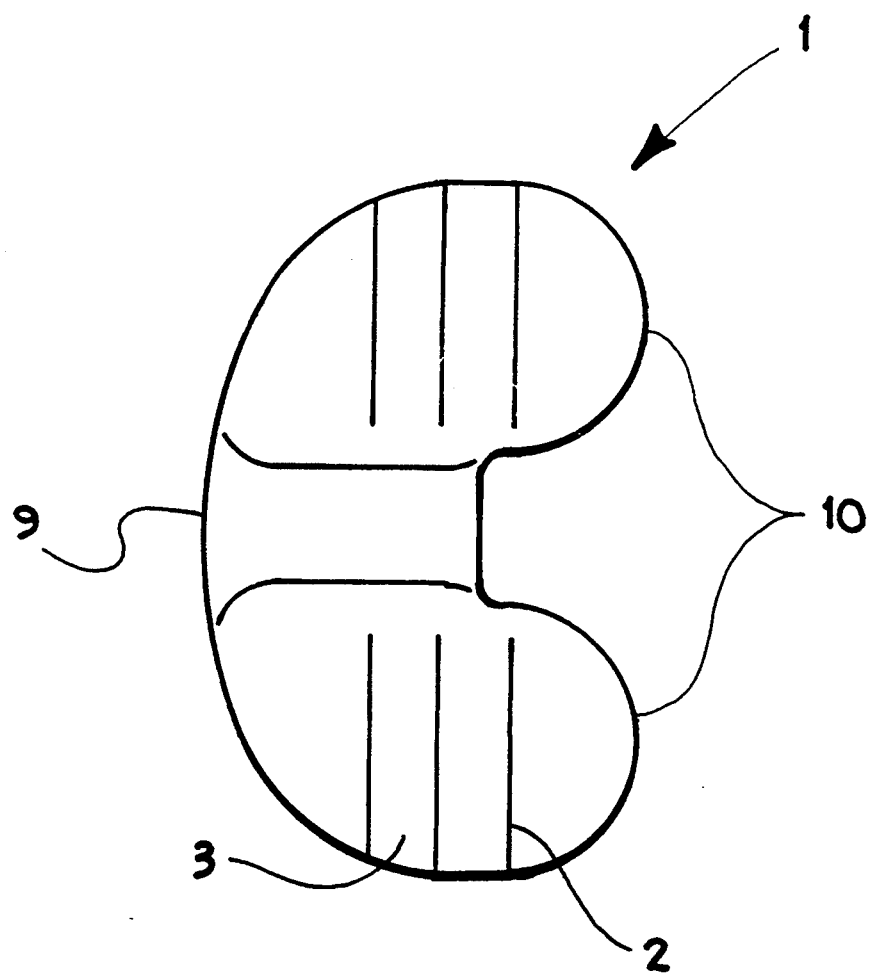
FIG. 1 is a plan view of the tibial knee component of this invention.
Figure 2:
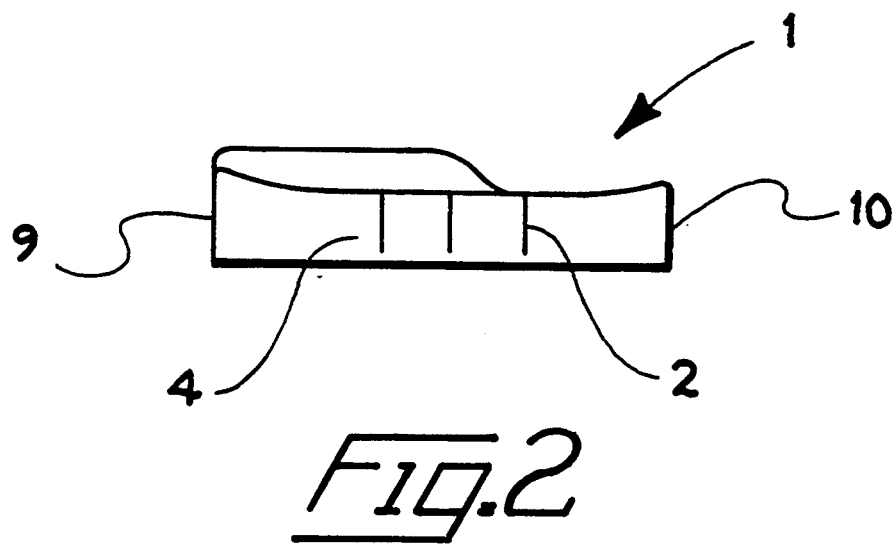
FIG. 2 is a side view of the component of FIG. 1.

Referring to FIGS. 1-2, a tibial component 1 of an artificial knee joint has a superior surface 3, an anterior surface 9, a posterior surface 10 and medial and lateral surfaces or sides, one 4 of which is indicated. The tibial component 1 includes reference marks 2 which preferably extend across at least part of the superior surface 3 and down at least one of the sides 4 of the tibial component. It has been found that three marks.6 spaced approximately 5 mm apart and located midway between the anterior and posterior surfaces of the tibial component work well. These marks are preferably located on both sides of the tibial component as shown. Such marks are made by any appropriate method such as by engraving or where the parts are molded by incorporating the marks into the mold.

Figure 3:
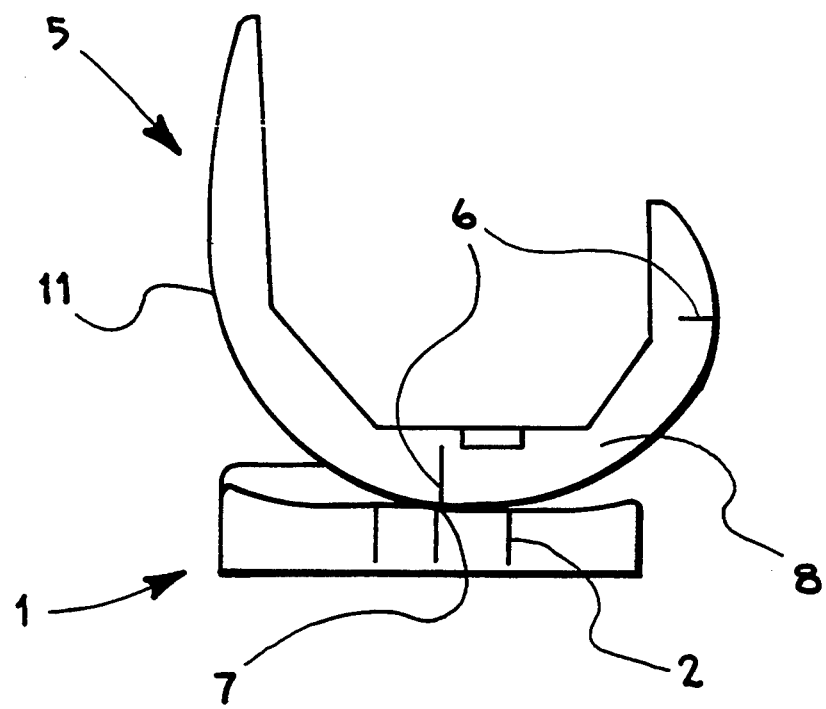
FIG. 3 is a side view of the tibial knee component of FIG. 1 and a femoral knee component with the components positioned as they would be at full extension in vivo.
Figure 4:
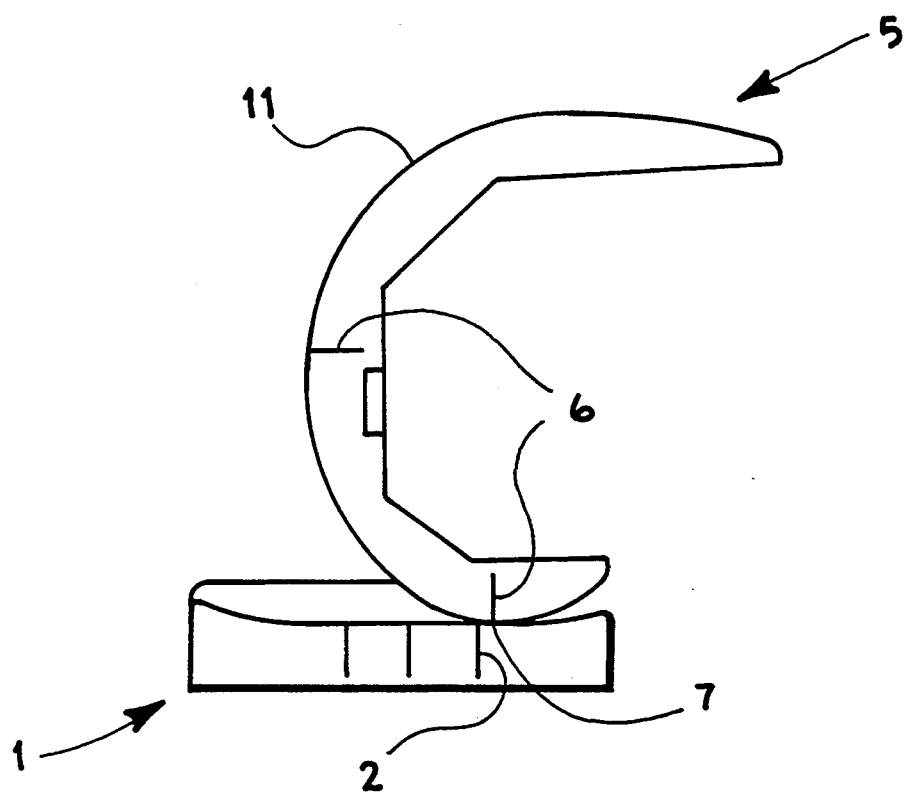
FIG. 4 is side view of the components of FIG. 3 with the components positioned as they would be at 90 degrees of knee flexion in vivo.

FIGS. 3-4 depict a femoral component 5 having medial and lateral surfaces or sides, one 8 of which is indicated. The femoral component 5 includes reference marks 6 corresponding to selected flexion angles of the knee, for example zero degrees of flexion and 90 degrees of flexion as shown. These marks 6 are located radially with respect to the outer curvature, or articular surface 11, of the femoral component so as to approximate the contact point 7 between the femoral component 5 and the tibial component 1 at the selected flexion angles. These marks 6 are also made by an appropriate method such as by engraving.

In use, the surgeon would note the position of the contact point 7 with respect to the tibial component 1 at a predetermined angle of flexion by comparing the contact point 7 position to the reference marks 2 on the tibial component 1. This relative position gives the surgeon an indication of correct component alignment. In the preferred embodiment shown, the femoral component 5 contains reference marks 6 to aid in determining the contact point 7 at selected flexion angles, for example zero and ninety degrees of flexion. However, the contact point 7 may be determined without these marks 6 or at flexion angles between these marks by approximating its location visually and then referring to the tibial reference marks 2 to locate its relative position on the tibial component 1.

To determine rollback, the relative position of the contact point 7 on the tibia is compared at two different flexion angles. For example, in FIG. 3, the components are shown oriented at zero degrees of flexion. The surgeon would note the relative position of the components using the reference marks as described above and then reposition the knee to another flexion angle such as 90 degrees as shown in FIG. 4. The surgeon would again note the relative position of the components and compare this position to the prior one. The difference in the positions is the amount of rollback.

The preferred embodiment of the invention contains reference marks on both the medial and lateral sides of the tibial component so that the surgeon can determine component position from either side of the knee. Having marks on both sides also allows the surgeon to compare medial and lateral rollback which yields further information regarding joint function. Also, the invention described in this disclosure can be incorporated in actual implant components as well as provisional or trial components used for selecting the actual implant components to be used.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An apparatus for determining knee position during knee joint replacement comprising:
    a prosthetic tibial knee component having medial, lateral and superior tibial surfaces; and
    a femoral knee component, the superior tibial surface configured to accommodate articulation with the femoral knee component, wherein the medial and lateral tibial surfaces each contain at least three uniformly spaced tibial reference marks extending down the surface for visually indicating relative location between the tibial knee component and the femoral knee component.

2. The apparatus of claim 1 wherein the femoral knee component has medial, lateral and articular femoral surfaces the medial and lateral femoral surfaces containing femoral reference marks corresponding to zero degrees of flexion and ninety degrees of flexion, the marks being located radially with respect to the articular surface so as to indicate the contact point between the femoral component and the tibial component at zero and ninety degrees of flexion respectively, the tibial and femoral reference marks both being visible at at least one angle of flexion as the components articulate with respect to one another.

3. The apparatus of claim 1 wherein the tibial reference marks extend across part of the superior surface and down each of the medial and lateral surfaces.

4. The apparatus of claim 1 wherein the tibial reference marks are spaced approximately 5 mm apart.

* * * * *

UNITED STATES PATENT AND TRADEMARK OFFICE
CERTIFICATE OF CORRECTION

PATENT NO. : 5,443,518
DATED : August 22, 1995
INVENTOR(S) : Insall

It is certified that error appears in the above-indentified patent and that said Letters Patent is hereby corrected as shown below:

On the title page, item [73],
Delete "Zimmer, Inc., Warsaw, Ind." from the assignee field

Signed and Sealed this

Twenty-fifth Day of March, 1997

Attest:

BRUCE LEHMAN

Attesting Officer

Commissioner of Patents and Trademarks